United States Patent
Aschl et al.

(10) Patent No.: US 12,366,567 B2
(45) Date of Patent: Jul. 22, 2025

(54) METHOD FOR DETERMINING TRACE METALS IN SILICON

(71) Applicant: Wacker Chemie AG, Munich (DE)

(72) Inventors: Waltraud Aschl, Julbach (DE); Theresa Kautnick, Burghausen (DE); Manuel Stadlmayr, Waldkraiburg (DE); Peter Steinkress, Braunau (AT)

(73) Assignee: Wacker Chemie AG, Munich (DE)

( * ) Notice: Subject to any disclaimer, the term of this patent is extended or adjusted under 35 U.S.C. 154(b) by 757 days.

(21) Appl. No.: 17/770,633

(22) PCT Filed: Jul. 21, 2020

(86) PCT No.: PCT/EP2020/070562
§ 371 (c)(1),
(2) Date: Apr. 21, 2022

(87) PCT Pub. No.: WO2022/017586
PCT Pub. Date: Jan. 27, 2022

(65) Prior Publication Data
US 2022/0381761 A1    Dec. 1, 2022

(51) Int. Cl.
*G01N 33/2045* (2019.01)
*C30B 29/06* (2006.01)
*G01N 1/32* (2006.01)

(52) U.S. Cl.
CPC ......... *G01N 33/2045* (2019.01); *C30B 29/06* (2013.01); *G01N 1/32* (2013.01)

(58) Field of Classification Search
CPC .......... C30B 13/28; C30B 29/06; G01N 1/32; G01N 33/2045
See application file for complete search history.

(56) References Cited

U.S. PATENT DOCUMENTS

2012/0060562 A1*  3/2012  Wochner ................. C01B 33/02
                                                          65/472

FOREIGN PATENT DOCUMENTS

| CN | 101131371 A | 2/2008 |
| DE | 102010039755 A1 | 3/2012 |
| EP | 0349117 A2 | 1/1990 |

(Continued)

OTHER PUBLICATIONS

W. Zulehner: "Historical overview of silicon pulling development", Materials Science and Engineering: B73, 2000, p. 7-15, Elsevier.

(Continued)

*Primary Examiner* — Jennifer Wecker

(57) ABSTRACT

A method for determining an amount of metallic impurities within silicon. The method includes the steps of (a) providing a rodlike silicon sample and a rodlike seed crystal in a zone melting apparatus, (b) zone melting to form a single silicon crystal having a conical end region with a droplike melt forming at the end of the single silicon crystal in a separation step, (c) cooling of the droplike melt to form a solidified silicon drop, (d) partial or complete dissolution of the silicon drop in an acid, and analyzing the solution obtained in step (d) by a trace analysis technique. Wherein the separation step further includes a remelting step for the silicon sample to reduce its diameter, forming a droplike melting zone, and separation of the seed crystal and the silicon sample by moving the seed crystal and the silicon sample apart from one another.

15 Claims, 3 Drawing Sheets

(56) References Cited

FOREIGN PATENT DOCUMENTS

| JP | 11-304791 A | 11/1999 |
|----|-------------|---------|
| TW | 201022491 A | 6/2010 |
| TW | 201527731 A | 7/2015 |

OTHER PUBLICATIONS

K. Graff: "Metal Impurities in Silicon-Device Fabrication", Springer Series in Material Science 24, 1995.
W. Keller: "Floating-Zone Silicon", Preparation and Properties of Solid State Materials, vol. 5, Marcel Dekker Inc., 1981.

* cited by examiner

METHOD FOR DETERMINING TRACE METALS IN SILICON

CROSS-REFERENCE TO RELATED APPLICATIONS

This application is a U.S. National Phase application of PCT Application No. PCT/EP2020/070562 filed on Jul. 21, 2020 the disclosure of which is incorporated by reference herein in its entirety.

The invention relates to a method for determining metallic impurities in silicon.

Polycrystalline silicon (polysilicon) is employed as a starting material in the production of monocrystalline silicon, for example by means of crucible pulling (Czochralski process) or by means of zone melting (float-zone process). The monocrystalline silicon can be saw-sliced into wafers and, after a multiplicity of further machining steps, can be used in the semiconductor industry for the fabrication of electronic components (e.g. resistors, diodes, bipolar transistors and MOS transistors). These machining steps generally include a deliberate and locally confined introduction of dopant impurities into the monocrystalline silicon. These dopants include, in particular, atoms having three or five valency electrons—that is, for example, the elements of main groups 3 and 5 of the Periodic Table. A precondition for the fabrication of these semiconductor elements is therefore that the silicon used is present in extremely high purity (no extraneous doping) and in the form of a perfect single crystal, since grain boundaries and lattice defects are among the possible causes of unwanted current paths. For the various applications of polysilicon, there are predefined specifications in relation to the impurities that must not be exceeded.

In principle, impurities (boron, phosphorus and arsenic, for example) in the ppt range (parts per trillion, $10^{-12}$) may already alter the desired performance of silicon semiconductors. Besides the doping atoms, trace metal impurities and non-metal impurities in particular may also contribute to defects. Examples here would include the non-metals carbon and chlorine, and metallic impurities will include iron, chromium, nickel or copper.

In order to ensure that the impurities are lower than mandated by the specification, an appropriately sensitive analytical method is needed. Furthermore, for routine monitoring of the impurities, practical aspects such as analysis duration and reproducibility are important.

Among metallic impurities, a fundamental distinction is made between metals which are present on the surface of the polysilicon and metals which are located in the bulk of the polysilicon. The text below deals with a method for determining metallic impurities in the silicon bulk.

One known method is that of instrumental neutron activation analysis (INAA). With this method, polysilicon samples, after treatment of their surface with a cleaning etch, are irradiated in a nuclear reactor. The metallic contaminations are transformed in this environment into radioactive isotopes. The element-specific gamma radiation which arises from the decomposition of the radioactive nuclei is measured and can be assigned to the elements.

INAA has the advantage that it possesses very low detection limits for the majority of metals. For Fe, Cr and Ni, these limits are typically less than or equal to 50 pg/g [pptw] silicon. For other metallic impurities, such as Ca or Ti, the detection limits are 500 to 2000 pg/g. A disadvantage is the great cost and complexity of instrumentation, as a neutron source (nuclear reactor or particle accelerator) is required. A further disadvantage is the need for a number of measurements staggered over time, as different elements possess different decomposition times. The duration of an INAA may be 2 to 3 months. Despite its high detection power, INAA is unsuitable as an in-process analytical technique (e.g. routine analyses to optimize parameters), for which short measurement durations are desirable. Moreover, this analysis is very expensive.

Another technique is that of dissolving a silicon sample without concentrating the impurities beforehand. In this case, the sample is dissolved completely in an aqueous etch solution composed of concentrated nitric acid ($HNO_3$) and hydrofluoric acid (HF), the matrix is smoked off, and the metallic traces are taken up again in a dilute acid. The sample can then be subjected to a trace analysis method, examples being atomic absorption spectrometry (AAS), mass spectrometry with inductively coupled plasma (ICP-MS), and optical emission spectrometry with inductively coupled plasma (ICP-OES).

The advantage lies in the short analytical run time of typically 1 to 2 days. Because the method does not entail a concentration step, the detection limits are customarily greater by a factor of 100 in comparison to INAA.

A further technique is known from EP 0 349 117 A2 as the "freeze-tip" method. In this case, the metallic impurities in a silicon rod, in the first step, are carried by zone melting (zone pulling) in the melt of the rod and are concentrated. At the end of zone melting, the energy supply is halted and the melt is solidified. The cooled section with the concentrated impurities is separated from the resultant single crystal and dissolved completely in an aqueous acid. This solution can then be analysed by one of the trace analysis methods stated.

One advantage of the "freeze-tip" method is its run time of typically less than a week, which is suitable for routine analyses. A disadvantage is that the melt or tip cools spontaneously and the crystallization state which forms is therefore undefined. A particular reason for this is the only partial segregation, and it leads to an uneven distribution of the metallic contaminations within the solidified silicon. Another disadvantage is the need for mechanical separation of the cooled tip from the single crystal. This is done using, for example, diamond saws, diamond cutters or tongues, which results generally in instances of metallic contamination that must be eliminated prior to dissolution. This elimination takes place by surface etching, although inevitably parts of the tip to be analysed are also removed and are lost from the actual trace metal analysis. This distorts the analytical outcome.

DE 10 2010 039 755 A1 likewise describes a method which is based on zone melting, where, in contrast to the "freeze-tip" method, specific pulling technology between the resultant single crystal and the silicon rod causes solidification of a droplike, crystalline sample section ("freeze-nub") at the end of the single crystal. An advantage of the method is that the nub does not have to be separated mechanically from the single crystal, thereby reducing contaminations and the loss of sample material. A disadvantage are the relatively low recovery rates, amounting to about 10-40%. The reason for this is the large fraction of silicon within the melt, which remains on the sample section at separation. This entails relatively high detection limits. The detection limit is calculated from the following formula:

$$DL = \frac{3\sigma RDV\left(\frac{ng}{ml}\right)100\%}{m_{Si}RR},$$

where
DL: Detection Limit,
RDV: Redissolution Volume,
RR: Recovery Rate,
$m_{Si}$: mass of remelted silicon
σ: standard deviation of the blank values Since the recovery rate is in the denominator formula, a low recovery rate becomes a high detection limit. Furthermore, the freeze nub is completely dissolved, requiring relatively large quantities of acid. This as well results in higher detection limits, since the acid contains impurities.

The object of the invention was to provide an improved method for determining the purity of silicon.

The object is achieved by means of a method for determining metallic impurities (trace metals and trace semimetals) in silicon, comprising the following steps:
 a) provision of a rodlike silicon sample and a rodlike seed crystal in a zone melting apparatus;
 b) zone melting (zone pulling) to form a single silicon crystal having a conical end region, with a droplike melt forming at the end of the single silicon crystal in a separation step;
 c) cooling of the droplike melt to form a solidified silicon drop (pin nub);
 d) partial or complete dissolution of the silicon drop in an acid;
 e) analysis of the solution obtained in step d) by a trace analysis technique.

The method is distinguished by the separation step in method step b) comprising the following chronological substeps:
 remelting of the silicon sample to reduce its diameter, where for a first time interval the direction of movement of the silicon sample and of the seed crystal is reversed relative to its previous direction of movement, to form the conical end region;
 formation of a droplike melting zone, where for a second time interval the movement of the seed crystal is halted and the direction of movement of the silicon sample is reversed again;
 separation of seed crystal and silicon sample, where the direction of movement of the silicon sample is reversed and said sample for a duration of 5 to 20 s has a speed of movement of 150 to 400 mm/min.

The method of the invention represents in particular a forward development and improvement of the method described in DE 10 2010 039 755 A1.

The silicon may be monocrystalline, multicrystalline and polycrystalline silicon. Preferably it is polycrystalline silicon, and more particularly has been produced by the Siemens process.

Zone melting (also referred to as zone pulling or the floating-zone (FZ) process) in a zone melting apparatus is familiar from the prior art. Reference may be made here in particular to the review article *Historical overview of silicon pulling development* (W. Zulehner—Materials Science and Engineering: B, 3 Apr. 2000, pp. 7-15, Elsevier) and to DE 10 2010 039 755 A1.

Briefly summarized, a rodlike silicon sample (drill core) is commonly first taken by core drilling. This core comes more particularly from a polysilicon rod produced according to the Siemens process. The silicon sample typically has a length of 3 to 25 cm, preferably of 5 to 15 cm, and a diameter of 10 to 50 mm, preferably of 15 to 25 mm, and more preferably of 17 to 21 mm.

Before being clamped into the zone melting apparatus, the silicon sample is commonly cleaned (treatment with solvent and/or acid). In the case of zone melting, the silicon sample is melted in a narrow zone at one end by an induction coil (induction heating). The melted zone (melt) is brought into contact with a rodlike single silicon crystal, onto which it grows, adopting the structure of the crystal thereof. This melting zone is then slowly moved through the rodlike silicon sample. In other words, the direction of movement of both rods is controlled such that the melting zone (induction coil) moves along the silicon sample. During this procedure, therefore, the direction of movement of the two rods is the same (cf. FIG. 1). As a result of different speeds of movement of the silicon sample and of the growing single crystal, a conical end region of the single crystal is maintained. So that the zone melts uniformly, the two rods rotate.

Based on its cylindrical region, as a function of the diameter of the silicon sample, the resultant single crystal has a diameter of typically 5 to 50 mm, preferably of 8 to 25 mm, more preferably of 10 to 15 mm. The crystal length is generally dependant on the diameter and on the length of the silicon sample.

It has emerged that in comparison to the freeze-nub method according to DE 10 2010 039 755 A1, the recovery rate goes up if the diameter of the silicon sample in its end region is reduced by remelting before the droplike melting zone is formed.

In the case of the freeze-nub method, at the moment of separation, there is a droplike melting zone between the silicon sample and the single crystal. On separation, the main part of this droplike melting zone (around 50% to 80%) recrystallizes on the silicon sample, with only 20% to 50% recrystallizing on the single crystal in the form of the nub. The fraction which recrystallizes on the silicon sample is lost to the analysis. In order to reduce this fraction, the method of the invention reduces the diameter of the end region of the silicon sample. In other words, the diameter of the area of the silicon sample in contact with the droplike melting zone is reduced. To achieve this, the direction of movement of the single crystal and of the silicon sample is reversed in comparison to the above-described normal course of zone melting. For an interval of time, therefore, the silicon sample is moved away from the droplike melting zone or the induction coil, leading to the reduction in the diameter in the end region of the silicon sample.

Surprisingly it has emerged that as a result of this measure, the metallic impurities are recovered in the solidified silicon drop (nub) in a fraction of up to 95%. By comparison with this, the freeze-nub method has an average recovery rate of only around 40%.

After the remelting, the silicon sample in an end region of length l preferably has a diameter which is less than or equal to the diameter of the single crystal at its contact face with the melt.

The diameter of the contact face of the single crystal with the melt is preferably 3 to 8 mm, more preferably 4 to 6 mm. The diameter of the silicon sample in its end region of length l is preferably 2 to 8 mm, more preferably 3 to 6 mm. In particular, both the diameter of the contact area of the single crystal and that of the end region of length l are around 5 mm (±0.5 mm).

The length l of the end region of the silicon sample preferably corresponds to one to three times its diameter.

During remelting, the silicon sample is preferably moved at a higher speed than the single crystal. The speed of movement of the single crystal preferably corresponds to about half the speed of the silicon sample.

The speed of movement of the silicon sample may be 5 to 15 mm/min, preferably 7 to 13 mm/min, more preferably 9 to 11 mm/min.

The speed of movement of the single crystal may be 2 to 10 mm/min, preferably 3 to 8 mm/min, more preferably 4 to 6 mm/min.

The first time interval during remelting, in which there is a reversal of the direction of movement, is preferably 30 to 300 s, more preferably 90 to 240 s, more particularly 90 to 120 s.

After the remelting, the droplike melting zone is formed. This is done by halting the movement of the seed crystal and synchronously reversing the direction of movement of the silicon sample again. The droplike melting zone is formed in a second time interval, which lasts preferably 1 to 4 s, more preferably 2 to 3 s. The speed of movement of the silicon sample here may be 1 to 5 mm/min, preferably 2 to 4 mm/min.

The seed crystal and silicon sample are separated slowly over a duration of 5 to 20 s, with a speed of movement of the silicon sample of 150 to 400 mm/min, preferably 250 to 350 mm/min, with the direction of movement being reversed again in comparison to the formation of the droplike melting zone, and with the single crystal continuing to be stationary (apart from the rotation). The induction heating is preferably switched off at the start of separation. After the separation, the droplike melting zone begins to cool.

It has emerged that as a result of the slow separation, all of the impurities present have already collected in an outer layer of the solidifying silicon drop (pin nub), and there is therefore no possible need for complete dissolution of the pin nub.

One possible explanation of this effect of the concentration of the metallic contaminations found in the outer marginal region might be a getter effect (cf. W. Zulehner—Materials Science and Engineering: B, 3 Apr. 2000, pp. 7-15, Elsevier). In this hypothesis, when the solid is cooled, metallic impurities dissolved in the solid at high temperatures undergo preferential precipitation at defect sites, and therefore accumulate at these defect sites. The surface of the pin nub, where the crystal lattice naturally ends and therefore carries open bonds on the surface, is one such defect site. The diffusion rate of the metallic impurities is generally a function of the temperature, and at high temperatures the diffusion is quicker than at low temperatures (cf. K. Graff, Metal Impurities in Silicon-Device Fabrication, ISBN 978-3-642-62965-5). A slow cooling phase of the pin nub might therefore boost the gettering (slow forward movement of the still-hot end of the silicon sample), with diffusion of the metallic impurities to the surface as a natural defect site of the silicon.

For the cooling in step c), it is also possible to halt the movement of the silicon sample and at the same time to place the single crystal into its original direction of movement (usual direction of movement in zone melting) at a speed of movement of 150 to 400 mm/min, preferably 250 to 350 mm/min. This may lead to additional boosting of the getter effect.

Generally speaking, however, the cooling in step c) may also be accomplished by simply leaving the sample to rest, with the rotation being switched off optionally.

The solidified silicon drop (pin nub) commonly has a diameter of 3 to 10 mm, preferably 6 to 8 mm. The pin nub usually corresponds to less than 1 wt % of the melted silicon sample. The weight of a pin nub (without the attaching single crystal) is typically 3 to 5 g.

As in the case of the freeze-nub method, there is no need for the pin nub to be separated from the single crystal for dissolution. After cooling, it is preferably transferred together with the single crystal into a dust-free bag. It can therefore be clamped contactlessly and hence free from contamination into a holding apparatus, and passed to a wet-chemical digestion procedure. The latter takes place preferably under clean-room conditions, with the pouch where appropriate being removed in the clean room.

Since the metallic impurities are located primarily in an outer layer of the pin nub, there is no need, with particular advantage, for the pin nub to be dissolved completely. It is sufficient instead to carry out incipient etching of the pin nub by temporary immersion in an etch solution (acid), with only a more or less thick outer layer dissolving, depending on the duration of immersion. It has emerged that for a pin nub weighing about 3 g, all of the metallic impurities are already contained in 0.1 to 0.2 g of silicon removal.

The immersion of the pin nub in the acid may optionally be preceded by removal-free surface cleaning, with dilute nitric acid, for example. It has emerged, however, that contamination of the sample is likely as a result of this procedure. Direct transfer to a dust-free pouch is preferred.

The immersion of the pin nub in the acid takes place preferably for a duration of 3 to 15 min, more preferably of 5 to 10 min, more particularly of about 6 min. In comparison to this, the etch time for complete dissolution of a freeze nub is on average 2 hours. A reduced etch time generally implies better blank values and hence improved detection limits. The longer the samples and the acid are exposed to the surrounding environment, the greater the likelihood that they will be contaminated.

The acid or etch solution preferably comprises a mixture of concentrated nitric acid (50-80 wt %) and hydrofluoric acid (20-50 wt %) in a ratio of 4:1 to 3:1, preferably 2:1 to 1:1. The etch solution may be used at room temperature or in heated form (e.g. 60° C.). With preference no heating is carried out. Transfer to a heating apparatus constitutes a further source of contamination.

Generally speaking, the amount of acid is selected such that it is just sufficient to dissolve an outer layer of the pin nub. A total amount of etch solution of 5-10 ml is typically employed. In order to decouple the detection limits of the impurities present from the influence of chemicals, the amount of chemical used ought in principle to be minimized. The pin-nub method is advantageous in this respect over the freeze-nub method.

The partial dissolution of the pin nub is accomplished preferably as follows:
1. provision of the etch solution,
2. immersion of the pin nub in the etch solution for 3-15 min,
3. rinsing of the pin nub removed from the etch solution, with fresh etch solution,
4. concentration of the etch solution by heating to 100 to 350° C.

Depending on the trace analysis measurement technique used subsequently, the metallic traces remaining after the concentration process are redissolved in dilute nitric acid (0.5 to 5 wt %) and/or dilute hydrofluoric acid to give a measurement solution. As a result of the reduced etch removal and of the consequently reduced silicon matrix (dissolved silicon is present in the form of hexaflourosilicic acid in the etch solution), the redissolution volume in the measurement solution has been able to be reduced by on average half (typically from 3 to 1.5 ml) by comparison with the freeze-nub method, thereby increasing the concentration of the metallic impurities. Measurement can therefore be carried out at greater concentrations, leading to more stable measurement outcomes, since the signal is increased in relation to the noise.

For the analysis in step e) it is possible to use customary mass spectrometers such as ICP-MS. Other preferred measurement techniques are atomic absorption spectrometry with electrothermal heating (known as graphite furnace atomic absorption spectrometry, GFAAS) and total reflection x-ray fluorescence analysis (TRFA).

Figure 1:
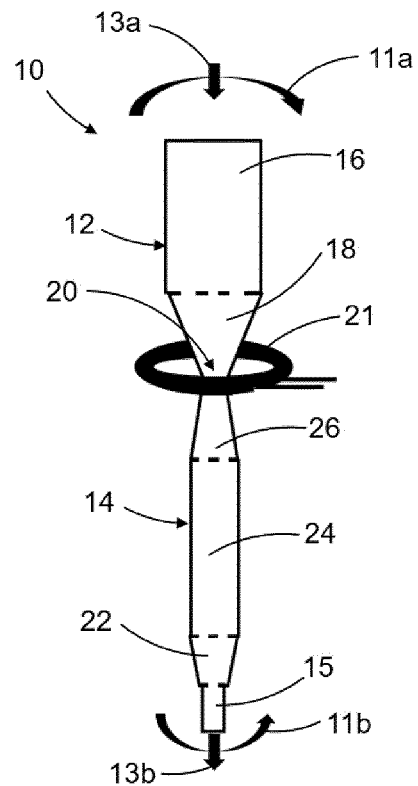
FIG. 1 shows the zone melting before the separation step according to the prior art.

FIG. 1 shows schematically a zone melting apparatus 10 with a silicon sample 12 and a single crystal 14, which are present shortly before the separation step. The silicon sample 12 and the single crystal 14 are each clamped into a rotating shaft, which for reasons of clarity is not illustrated. The direction of rotation is indicated by the arrows 11a, 11b, the direction of movement by the arrows 13a, 13b. The silicon sample 12 and the single crystal 14 are joined to one another via a melting zone 20, which is heated by an induction coil 21. The silicon sample 12 is a rodlike polysilicon sample having a cylindrical region 16 and a conical region 18 in the melting zone 20. The original length of the polysilicon sample was about 15 cm. The diameter of the region 16 is about 20 mm. The single crystal 14 recrystallized on a single seed crystal 15 consists of an initial cone 22, a cylindrical section 24, and a conical section 26 in the melting zone 20. The length of the single crystal 14 is around 110 mm, and the diameter in the cylindrical section 24 is about 14 mm.

Figure 2:
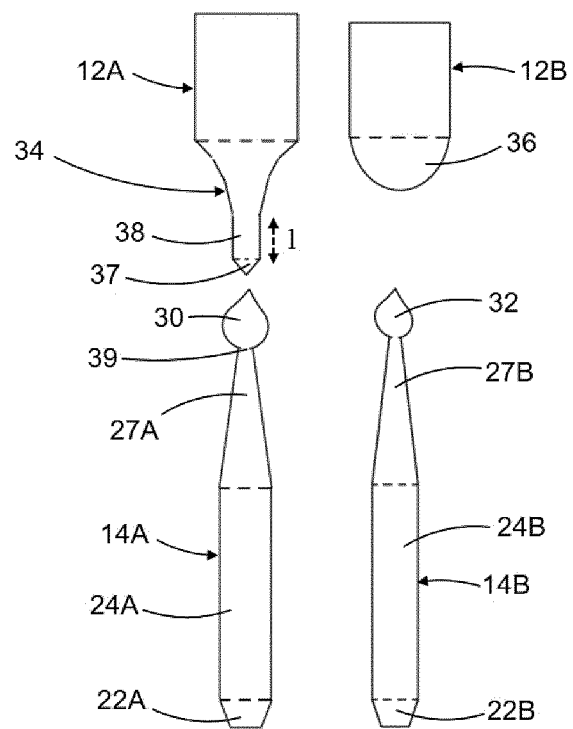
FIG. 2 shows a comparison between pin-nub and freeze-nub methods.

FIG. 2 shows a pin nub 30 on a conical end region 27A of a single crystal 14A which has been produced according to the method of the invention. Illustrated in comparison to this is a freeze nub 32 (according to DE 10 2010 039 755 A1) on a conical end region 27B of a single crystal 14B. The end regions 27A, 27B may have a length of 3 to 6 cm. The numbering of elements already identified in FIG. 1 is retained, with elements from the pin nub method being distinguished by an "A" and elements from the freeze nub method by a "B". The corresponding silicon samples 12A and 12B, with their end regions 34 and 36 resulting from the methods, are likewise illustrated. There are no substantial differences in the shape of the single crystals 24A, 24B. There is not necessarily any difference in the diameter of the cylindrical sections 24A, 24B. The essential visible difference after the implementation of both methods lies in the end regions 34, 36 of the single crystals 12A, 12B. In the case of implementation of the freeze-nub method, the part of the silicon sample 12B that is located in the melt during separation forms an end region 36 which is like a round head. This end region 36 corresponds in general to 50-80% of the melt. Hence only 20-50% remains in the form of the freeze nub 32 at the conical end region 27B of the single crystal 24B. Conversely, in the case of the pin-nub method, as a result of the remelting, an end region 34 is formed with a partial section 38 having a length l, which in terms of diameter corresponds at most to the diameter of a contact face 39 between the conical end region 27A and pin-nub 30. In this way, the part of the silicon sample 12A that is located in the melt during separation is reduced to a small fraction 37. This fraction 37 corresponds customarily to only 5-10% of the melt during the separation procedure. Commonly, thus, only 5-10% of silicon melt is lost to the analysis.

Figure 3:
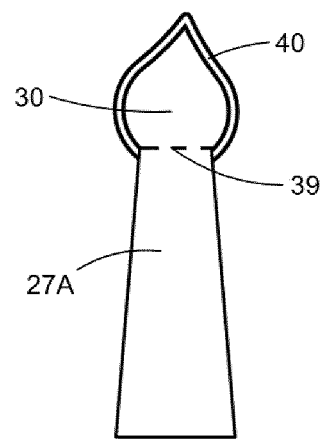
FIG. 3 shows a pin-nub on a single crystal.

FIG. 3 shows a pin-nub 30 which has formed, after the cooling, on the conically tapering end region 27A of the single crystal 14A (cf. FIG. 2). An outer layer 40 which has been marked is intended to illustrate approximately the etch removal, which is provided for the subsequent analysis on partial dissolution of the silicon drop in an acid. The metallic impurities are contained in this outer layer 40. The diameter of the contact face 39 with the pin-nub 30 is about 5 mm. This diameter also corresponds essentially to the diameter of the contact face of the single crystal 14A in its conical end region 27A with the melt at the moment of separation.

Figure 4:
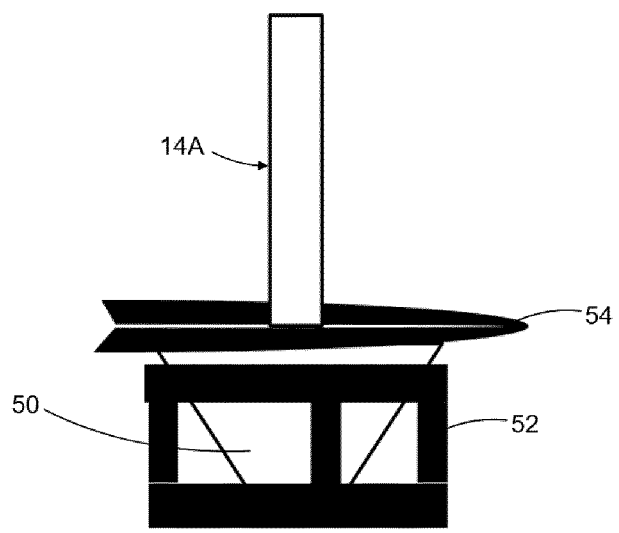
FIG. 4 shows a pin-nub in an acid bath.

FIG. 4 shows a conical, acid-filled vessel 50 in a mount 52. The single crystal 14A with the pin-nub is immersed in the vessel 50, where it is secured by a holding bracket 54. As a result of the conically tapering vessel, the amount of acid used for the partial dissolution can be reduced.

EXAMPLE 1

6 drill cores (silicon samples) all having a diameter of 22 mm and a length of around 8 cm were taken from a silicon rod pulled using the Czochralski process and contaminated with a known contamination with the metals Fe, Cr, Ni, Cu, Zn and Sn. The samples were etched with a cleaning etch for about 15 min in an acid mixture of HF (45%) and $HNO_3$ (65%) in a ratio of 1:6, and were rinsed with ultra-pure water. Preparation for this purpose took place under cleanroom conditions (class 10).

The silicon samples were each installed into an FZ apparatus (upper pulling shaft: silicon sample; lower pulling shaft: seed). The seed used was a single silicon crystal. The zone melting operation is set out in Table 1, with reference also being made to the figures. Speeds v of movement that are labelled with a negative sign indicate the usual pulling direction when the melting zone is moved through the silicon sample. Referring to FIGS. 1 and 2, a negative speed of movement denotes a downward movement of the single crystal 14A and/or of the silicon sample 12A in relation to the induction coil 21. A positive sign indicates an upward movement.

TABLE 1

| Step | Pin-nub method |
|---|---|
| Preheating | The Si sample 12A is heated using a preheater Generator power (P): 36 kW (70% power) |
| Coupling-in | Induction power couples in Melt drop is formed on the Si sample 12A |
| Attachment | Melt drop is joined to the seed at the level of the induction coil 21 (the two pulling shafts are moved toward one another manually) |
| Formation of initial cone 22 | Parameters for cylindrical section 24 diameter of 14 mm: P = 14 kW (40% power) v top pulling shaft: −2.4 mm/min v bottom pulling shaft: −5.8 mm/min Pulling length (travel of bottom pulling shaft): 5 mm |
| Cylindrical section 24A | P = 14.2 kW (40.5% power) v top pulling shaft: −2.4 mm/min v bottom pulling shaft: −6.0 mm/min Length: (travel of bottom pulling shaft): 70 mm Diameter: 14 mm |
| Transition to region 27A | Step 1: P Generator: 13.7 kW (39.0% power) v top pulling shaft: −1.8 mm/min v bottom pulling shaft: −10.0 mm/min Pulling length (travel of bottom pulling shaft): 10 mm |

TABLE 1-continued

| Step | Pin-nub method |
|---|---|
| | Step 2:<br>P = 13.5 kW (38.5% power)<br>v top pulling shaft: −1.2 mm/min<br>v bottom pulling shaft: −10.0 mm/min<br>Pulling length (bottom): 10 mm |
| Region 27A | P = 13.3 kW (38% power)<br>v top pulling shaft: −1.0 mm/min<br>v bottom pulling shaft: −14.5 mm/min<br>Pulling length (travel of bottom pulling shaft): 22 mm<br>Diameter of contact face 39: 5-6 mm |
| Remelting | P = 13.3 kW (38% power)<br>v top pulling shaft: +10 mm/min<br>v bottom pulling shaft: +6 mm/min<br>Travel of bottom pulling shaft: 8 mm<br>Diameter of partial section 38: 5-6 mm |
| Formation of pin-nub 30 | P = 13.7 kW (39% power)<br>v top pulling shaft: −2.0 mm/min<br>v bottom pulling shaft: 0 mm/min<br>Pulling length (travel of bottom pulling shaft): 0 mm |
| Separation | P = 0 kW<br>v top pulling shaft: +350 mm/min<br>v bottom pulling shaft: 0 mm/min<br>Travel of top pulling shaft: 40 mm<br>Travel of bottom pulling shaft: 0 mm |
| Cooling | Step 2:<br>P = 0 kW<br>v top pulling shaft: 0 mm/min<br>v bottom pulling shaft: −350 mm/min<br>Travel of top pulling shaft: 0 mm<br>Travel of bottom pulling shaft: 300 mm |

The rotary speed of the single crystal 14A was typically from 15 to 30 rpm, and that of the silicon sample 12A was typically from 3 to 10 rpm in the opposed direction of rotation (cf. FIG. 1, arrows 11A, 11B). After separation and cooling, the largest diameter of the pin-nub was around 8 mm.

After dismounting, the pin-nub 30 was transferred with a holding bracket 54 into an acid-filled conical vessel 50 of perfluoroalkoxyalkane (PFA) under clean-room conditions (class 10) and partially dissolved (partially etched). The acid consisted of a mixture of $HNO_3$ (69 wt %) and HF (40 wt %) in a ratio of 1:1. The vessel 50 was filled with around 6 ml of acid. The fully immersed pin-nub was exposed to the acid for 6 min. The pin-nub was subsequently washed with 1 ml of fresh acid. The etched solution obtained was then concentrated at a temperature of 250° C. for around 30 min. The residue obtained was dissolved with a mixture of 25 μl of HF (40 wt %), 25 μl of $HNO_3$ (65 wt %) and 1450 ml of ultra-pure water to give a measurement solution. This treatment was carried out with each of the six pin-nubs obtained.

On measurement by means of ICP-MS, determinations were made of the elements Fe, Cr, Ni, Na, K, Sn, Zn, Al, Cu, Mo, La, Cs, Ce, Te, Sc, Se, Ti, Ta, Ge, W, Mg, Ag, Li, V, Mn, Zr, Pb, Y, Sr, Ba, Bi, Cd, Sn, As, Ru, Rb, U, Ga, In, Ca and Co. Blank values were generated as well. For this purpose, 4 conical vessels were filled with acid and processed analogously without samples. The amounts measured in the context of these blank values were averaged and subtracted in each case from the amounts measured for the samples. The calculated value was then expressed relative to the total weight of the single crystal.

This shows significantly higher recovery rates (RR) for selected metals in comparison to the freeze-nub method. The values in question are average values from all six silicon samples.

TABLE 2

| | RR in % | | | | | |
|---|---|---|---|---|---|---|
| | Fe | Cr | Ni | Cu | Zn | Sn |
| Freeze-Nub | 37 | 40 | 54 | 38 | 37 | 41 |
| Pin-Nub | 94 | 95 | 95 | 96 | 94 | 94 |

Table 3 shows reduced detection limits in comparison to the freeze-nub method.

TABLE 3

| | DL (pg/g) | | | | | |
|---|---|---|---|---|---|---|
| | Fe | Cr | Ni | Cu | Zn | Na |
| Freeze-Nub | ≤20 | ≤20 | ≤20 | ≤10 | ≤10 | ≤20 |
| Pin-Nub | ≤2 | ≤1 | ≤1 | ≤1 | ≤1 | ≤1 |

Figure 5:
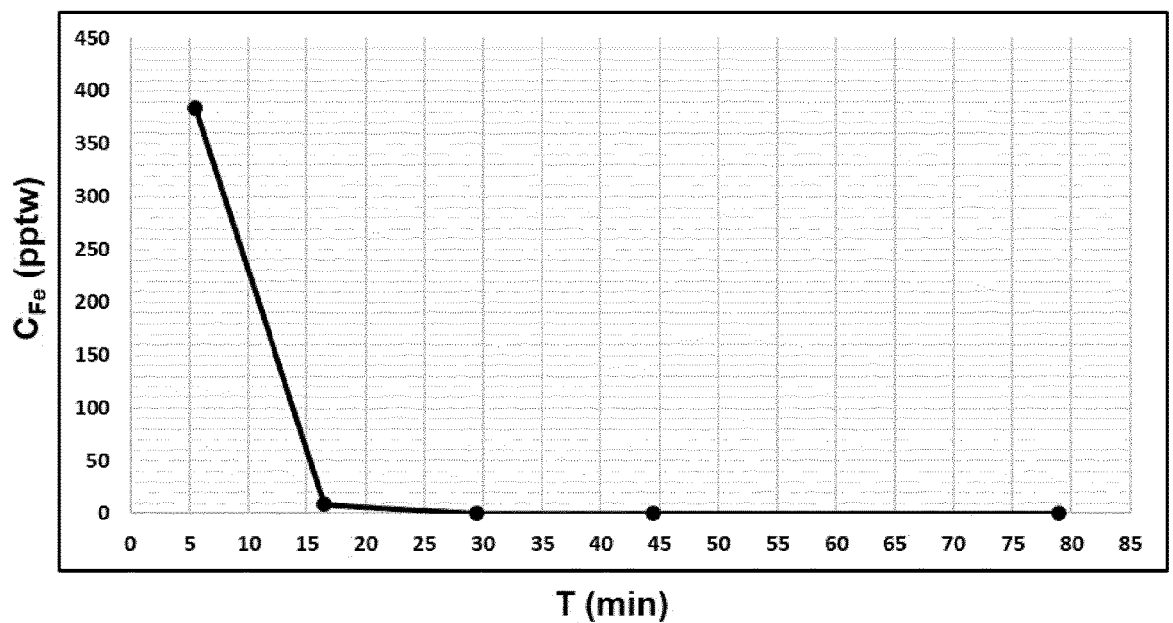
FIG. 5 shows the concentration of iron in a step etch.
Figure 6:
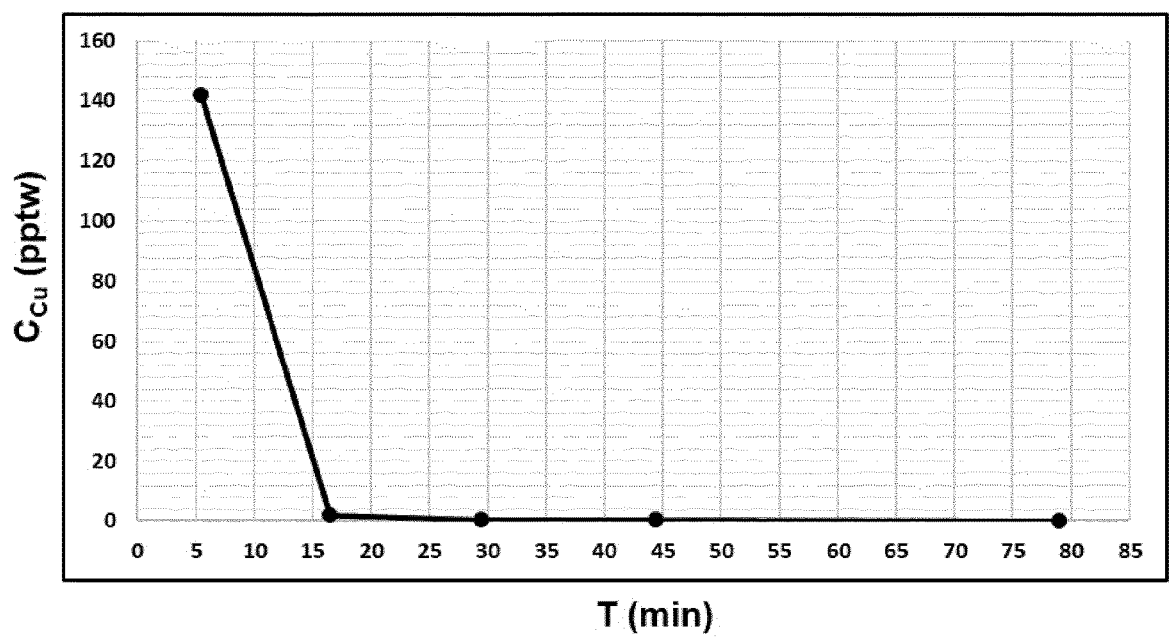
FIG. 6 shows the concentration of copper in a step etch.

FIGS. 5 and 6 show the concentration profile of iron ($C_{Fe}$, FIG. 5) and copper ($C_{Cu}$, FIG. 6) in measurement solutions obtained after 5 min, 16 min, 29 min, 44 min and 79 min of partial etching of a pin-nub (step etch: after each step, the pin-nub was transferred to fresh etch solution). Corresponding curves were prepared for chromium and nickel, with each experiment being repeated once (samples 1 and 2 in each case). The results are set out in Table 4.

TABLE 4

| | Etch removal per step in % | | | |
|---|---|---|---|---|
| | Fe | Cr | Ni | Cu |
| $1^{st}$ etching sample 1 | 98 | 96 | 98 | 98 |
| $2^{nd}$ etching sample 1 | 2 | 3 | 2 | 2 |
| $3^{rd}$ etching sample 1 | 0 | 0 | 1 | 0 |
| $4^{th}$ etching sample 1 | 0 | 0 | 0 | 0 |
| $5^{th}$ etching sample 1 | 0 | 0 | 0 | 0 |
| $1^{st}$ etching sample 2 | 98 | 97 | 98 | 98 |
| $2^{nd}$ etching sample 2 | 2 | 2 | 1 | 1 |
| $3^{rd}$ etching sample 2 | 0 | 1 | 0 | 0 |
| $4^{th}$ etching sample 2 | 0 | 0 | 0 | 0 |
| $5^{th}$ etching sample 2 | 0 | 0 | 0 | 0 |

After an etching time of just 5 min and a removal of only 0.06 g, at least 96% of the metallic impurities had been etched away in all cases. This result shows that by cleaning of a freeze tip (cf. EP 0 349 117 A2) with a cleaning etch, a portion of the metallic impurity is already lost to analysis.

EXAMPLE 2

Various Parameters were Tested in the Zone Melting:

7 silicon samples (drill cores) with 19 and 22 mm were used. By adapting the corresponding parameters in the zone melting, different diameters (D) were obtained on the single crystal and on the end region of the silicon samples. Moreover, different travel lengths of the lower pulling shaft were tested during remelting, and different pin-nub sizes were obtained. In addition, samples with different single crystal weights were pulled and tested. The results are summarized in Table 5.

TABLE 5

| # | Single crystal (D) mm | Sample section (D) mm | Remelted silicon g | Length of conical region mm | Length of remelts mm | (D) sample end on separation mm | Nub size g | RR (averages Fe, Cr, Ni, Cu) % |
|---|---|---|---|---|---|---|---|---|
| 1 | 12 | 22 | 30 | 30 | 8 | 4 | 0.4 | 97 |
| 2 | 12 | 19 | 20 | 30 | 8 | 4 | 0.3 | 94 |
| 3 | 14 | 22 | 30 | 35 | 8 | 4 | 0.5 | 95 |
| 4 | 15 | 22 | 20 | 50 | 8 | 3 | 0.4 | 97 |
| 5 | 10 | 22 | 40 | 20 | 8 | 3 | 0.4 | 96 |
| 6 | 14 | 22 | 50 | 30 | 5 | 5 | 0.4 | 94 |
| 7 | 10 | 22 | 15 | 30 | 15 | 8 | 0.4 | 90 |

The recovery rate was always between 90% and 97%.

The invention claimed is:

1. A method for determining an amount of metallic impurities within silicon, comprising the steps of: a) providing a rodlike silicon sample and a rodlike seed crystal in a zone melting apparatus; b) zone melting to form a single silicon crystal having a conical end region, with a droplike melt forming at the end of the single silicon crystal in a separation step; c) cooling of the droplike melt to form a solidified silicon drop; d) partial or complete dissolution of the silicon drop in an acid; and e) analyzing the solution obtained within step d) by a trace analysis technique; wherein the separation step further comprises the steps of: (i) remelting of the silicon sample to reduce its diameter, where for a first time interval the direction of movement of the silicon sample and of the seed crystal is reversed relative to its previous direction of movement, to form the conical end region; (ii) forming a droplike melting zone, where for a second time interval the movement of the seed crystal is halted and the direction of movement of the silicon sample is reversed again; and (iii) wherein during separation of seed crystal and silicon sample where the direction of movement of the silicon sample is reversed, and wherein said separation step occurs for a duration of 5 to 20 s, and has a speed of movement of 150 to 400 mm/min.

2. The method of claim 1, wherein after the remelting, the silicon sample in an end region of length l has a diameter which is less than or equal to the diameter of the single crystal at its contact face with the melt.

3. The method of claim 2, wherein the diameter of the contact face of the single crystal with the melt is 3 to 8 mm, preferably 4 to 6 mm.

4. The method of claim 2, wherein the diameter of the silicon sample in its end region of length l is 2 to 8 mm, preferably 3 to 6 mm.

5. The method of claim 2, wherein the length l of the end region of the silicon sample corresponds to one to three times its diameter.

6. The method of claim 1, wherein the silicon sample during remelting is moved at a higher speed of movement than the single crystal.

7. The method of claim 6, wherein the speed of movement of the silicon sample is 5 to 15 mm/min, preferably 7 to 13 mm/min, more preferably 9 to 11 mm/min.

8. The method of claim 6, wherein the speed of movement of the single crystal is 2 to 10 mm/min, preferably 3 to 8 mm/min, more preferably 4 to 6 mm/min.

9. The method of claim 1, wherein the first time interval during remelting lasts 30 to 300 s, preferably 90 to 240 s, more preferably 60 to 120 s.

10. The method of claim 1, wherein the formation of the droplike melting zone and a speed of movement of the silicon sample is 1 to 5 mm/min, preferably 2 to 4 mm/min.

11. The method of claim 1, wherein the second time interval lasts 1 to 4 s, preferably 2 to 3 s.

12. The method of claim 1, wherein the separation of seed crystal and silicon sample and a speed of movement of the silicon sample is 250 to 350 mm/min.

13. The method of claim 1, wherein the cooling of the droplike melt, the movement of the silicon sample is halted and the seed crystal is removed in its original direction of movement with a speed of movement of 150 to 400 mm/min, preferably 250 to 350 mm/min, from the silicon sample.

14. The method of claim 1, wherein the silicon drop is dissolved partially by immersion in the acid for a duration of 3 to 15 min, preferably 5 to 10 min.

15. The method of claim 14, wherein the acid comprises a mixture of concentrated nitric acid and hydrofluoric acid in a ratio of 4:1 to 3:1, preferably 2:1 to 1:1.

* * * * *